United States Patent [19]
Fuhr

[11] Patent Number: 5,954,674
[45] Date of Patent: Sep. 21, 1999

[54] APPARATUS FOR GATHERING BIOMECHANICAL PARAMETERS

[75] Inventor: Arlan W. Fuhr, Phoenix, Ariz.

[73] Assignee: Kinex IHA Corporation, Phoenix, Ariz.

[21] Appl. No.: 08/949,271

[22] Filed: Oct. 13, 1997

[51] Int. Cl.⁶ .................................................. A61B 5/00
[52] U.S. Cl. .......................................................... 600/594
[58] Field of Search .................................. 600/587, 594, 600/595

[56] References Cited

U.S. PATENT DOCUMENTS

| | | | |
|---|---|---|---|
| 3,608,541 | 9/1971 | Hall | 128/2 |
| 3,908,279 | 9/1975 | Yoslow et al. | 33/174 |
| 3,991,745 | 11/1976 | Yoslow et al. | 128/2 |
| 4,108,164 | 8/1978 | Hall, Sr. | 128/25 |
| 4,113,250 | 9/1978 | Davis | 272/93 |
| 4,146,311 | 3/1979 | Murr | 351/24 |
| 4,284,847 | 8/1981 | Besserman | 73/585 |
| 4,461,085 | 7/1984 | Dewar et al. | 33/174 |
| 4,462,252 | 7/1984 | Smidt et al. | 73/379 |
| 4,492,236 | 1/1985 | Pile | 128/781 |
| 4,528,990 | 7/1985 | Knowles | 128/782 |
| 4,565,368 | 1/1986 | Boettcher | 272/129 |
| 4,655,227 | 4/1987 | Gracovetsky | 128/781 |
| 4,664,130 | 5/1987 | Gracovetsky | 128/781 |
| 4,699,156 | 10/1987 | Gracovetsky | 128/781 |
| 4,702,108 | 10/1987 | Amundsen et al. | 73/379 |
| 4,732,381 | 3/1988 | Skowronski | 272/134 |
| 4,768,779 | 9/1988 | Oehman, Jr. et al. | 272/94 |
| 4,777,965 | 10/1988 | Allison et al. | 600/594 |
| 4,800,897 | 1/1989 | Nilsson | 128/782 |
| 4,805,455 | 2/1989 | DelGiorno et al. | 73/379 |
| 4,824,103 | 4/1989 | Smidt | 272/125 |
| 4,893,808 | 1/1990 | McIntyre et al. | 272/94 |
| 4,922,925 | 5/1990 | Crandall et al. | 128/782 |
| 4,928,709 | 5/1990 | Allison et al. | 600/595 |
| 4,971,069 | 11/1990 | Gracovetsky | 128/781 |
| 4,979,519 | 12/1990 | Chavarria et al. | 128/857 |
| 5,012,819 | 5/1991 | Marras et al. | 128/781 |
| 5,022,412 | 6/1991 | Gracovetsky et al. | 128/781 |
| 5,042,505 | 8/1991 | Mayer et al. | 128/781 |
| 5,082,001 | 1/1992 | Vannier et al. | 128/774 |
| 5,094,249 | 3/1992 | Marras et al. | 128/781 |
| 5,143,088 | 9/1992 | Marras et al. | 128/781 |
| 5,178,160 | 1/1993 | Gracovetsky et al. | 128/782 |
| 5,188,121 | 2/1993 | Hanson | 128/781 |
| 5,203,346 | 4/1993 | Fuhr et al. | 600/594 |
| 5,297,539 | 3/1994 | Liebl et al. | 601/26 |
| 5,324,247 | 6/1994 | Lepley | 482/134 |
| 5,337,758 | 8/1994 | Moore et al. | 128/781 |
| 5,373,858 | 12/1994 | Rose et al. | 128/782 |
| 5,425,378 | 6/1995 | Swezey et al. | 128/782 |
| 5,445,152 | 8/1995 | Bell et al. | 128/653.5 |
| 5,462,065 | 10/1995 | Cusimano | 600/595 |
| 5,513,651 | 5/1996 | Cusimano et al. | 128/782 |
| 5,524,645 | 6/1996 | Wills | 128/898 |
| 5,557,514 | 9/1996 | Seare et al. | 364/401 |
| 5,583,758 | 12/1996 | McIlroy et al. | 395/202 |
| 5,697,791 | 12/1997 | Nashner et al. | 434/247 |

FOREIGN PATENT DOCUMENTS

| | | |
|---|---|---|
| PCT/SE86/00304 | 1/1987 | WIPO . |
| PCT/SE88/00275 | 11/1989 | WIPO . |
| PCT/US91/01796 | 10/1991 | WIPO . |

OTHER PUBLICATIONS

Gilman, et al., "Instrumentation & Techniques: Measurement of Head Movement During Auditory Localization," *Behavior Research Methods & Instrumentation*, vol. 11(1), 1979, pp. 37–41.

(List continued on next page.)

*Primary Examiner*—Max Hindenburg

[57] ABSTRACT

A system for obtaining biomechanical data for the cervical spine of a subject is described. The system includes a display showing a figure representative of the subject. The figure may be displayed in substantially real time relative to the subject's movement The figure may be viewed from a selected one of a plurality of views.

11 Claims, 6 Drawing Sheets

OTHER PUBLICATIONS

Chao, et al., "Measurement of Neck Range and Pattern of Movement," *International Congress of Biomechanics, University of California, Los Angeles*, Abstract #319, XII, 1989.

Keshner, et al., "Actions of the Head and Neck During Postural Stabilization," *First World Congress of Biomechanics, University of California, San Diego*, vol. II, Aug. 30–Sep. 4, 1990, La Jolla, California, p. 208.

Peles, et al., "Organization of Neck Muscle Activity for Quast–Static and Dynamic 3–D Head Movements," *First World Congress of Biomechanics, University of California, San Diego*, vol. II, Aug. 30–Sep. 4, 1990, La Jolla, California, p. 208.

Winters, et al., "Relations Between Neck Muscle Activity and Screw Axis Parameters of the Head," *First World Congress of Biomechanics, University of California, San Diego*, vol. II, Aug. 30–Sep. 4, 1990, La Jolla, California, P. 209.

Triano, et al., "Neck Muscle Responses to Manipulation of the Cervical Spine," *First World Congress of Biomechanics, University of California, San Diego*, vol. II. Aug. 30–Sep. 4, 1990, La Jolla, California, p. 209.

Winters, et al., "Neck Muscle Activity and 3–D Head Kinematics During Quasi–Static and Dynamic Tracking Movements," *Multiple Muscle Systems: Biomechanics and Movement Organization*, 1990, pp. 461–480.

White, et al., *Clinical Biomechanics of the Spine*, Second Edition, pp. 92–115.

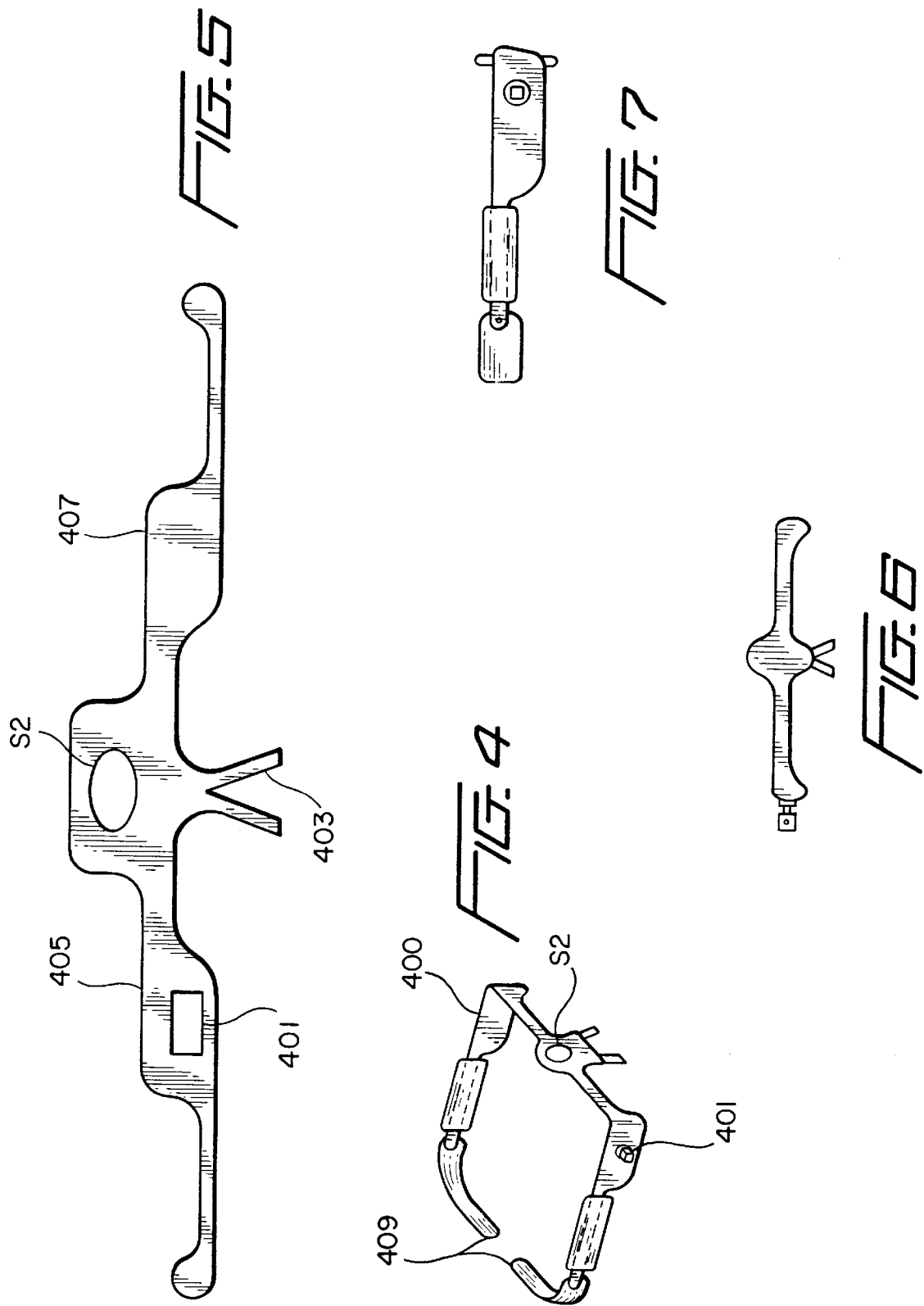

APPARATUS FOR GATHERING BIOMECHANICAL PARAMETERS

BACKGROUND OF THE INVENTION

This invention pertains to an apparatus for non-invasive determination of disorders of human joints, in general, and an apparatus for determining the dynamic biomechanical parameters of the cervical spine, in particular.

Analysis of neck injury caused by hyperextension of the head, often followed by strong flexion due to excessive acceleration and deceleration of the body has been lacking and the corresponding ability to diagnose the likelihood of injury as well as the specific location of injury has been limited. Injuries and disorders of the cervical spine often are soft tissue injuries and as such are not readily ascertainable by means of conventional diagnostic aids such as x-ray, MRI, CT-scan, or other tissue penetrating imaging devices. Consequently, the confirmation of neck injury tends to be a subjective diagnosis.

Even where it is indisputable that a patient has suffered an injury to the cervical spine, there is no objective determination available which will enable medical personnel to determine progress in recovery from the injury or effectiveness of different types of treatment of the injury. In addition, it would be desirable to have a clinical method for determining the status of an individuals cervical spine before, during and after engagement in specific activities. Yet even further, it may be desirable in certain circumstances to be able to determine the incidence of neck injury in certain populations of individuals.

Significant effort has been directed to the formulation of reliable techniques and apparatus for measuring movement of human body parts. In particular, U.S. Pat. No. 5,203,346 to Arlan W. Fuhr et al describes a method and apparatus for the non-invasive determination kinematic movement of the cervical spine. The Fuhr arrangement provides a non-invasive method and apparatus for determining a patient's three dimensional helical axis of rotation during specific movements. It is suggested in the Fuhr patent that the head axis of rotation is then used with normal data bases for diagnosis of abnormal kinematic function of the cervical spine.

In the illustrative embodiment described in the Fuhr patent, video cameras are utilized to record movement of markers carried on the patient's head as the patient moves his/her head through specific head movements. A head mounted light source acts as a pointer so that the patient receives instantaneous feedback as to the position of his head. A planar array of vertical, horizontal and oblique oriented lines is placed on a wall. The array includes circular landmarks to depict specific angles. The patient is instructed to perform a series of voluntary range-of-motion tasks to provide the outside parameters of his/her range-of-motion for the actual test. The patient starts by making standard, voluntary, self-paced, slow range-of-motion movement in the flexion-extension (down-up), axial rotation (left-right), and lateral bending (side-to-side) directions. Following the voluntary range-of-motion tasks, the patient is instructed to follow target patterns within his/her voluntary range-of-motion. Four target patterns are used: left-right, up-down, a box pattern in either direction, and an oblique or x-shaped pattern.

While the patient is following the target pattern, movement of the markers are recorded on videotapes for further processing. Data recorded on the videotapes is processed to calculate various screw axis parameters and to plot same. The derived plots are then compared to standard plots and/or to prior plots of the same patient so that the nature and/or extent of the abnormal kinematic movement of the cervical spine can be determined.

Although the method and apparatus shown and described in the Fuhr patent has provided a significant advance in the ability to measure kinematic function of the cervical spine, the method and apparatus requires analysis of video taped motions of a each patient which takes a relatively long period of time to provide quantitative data. In addition, the apparatus and method of the Fuhr patent is principally for the determination of certain parameters.

It therefore is one object of the invention to provide a method with which the kinematic function of the cervical spine in a patient may be determined.

It is yet a further object of the invention to provide a method of determining normal or acceptable biomechanical parameters for cervical spine kinematic movement.

It is a further object of the invention to provide a method and apparatus which may on a non-invasive basis determine the health status of a patient's cervical spine.

These and other objects of the invention are provided by a method and apparatus in accordance with the invention as described herein.

SUMMARY OF THE INVENTION

Apparatus in accordance with the invention includes a display unit operable by a processing unit to display a figure representative of a patient or subject being tested. The display may be operated to display the figure in substantially real time to show the movement of the subject.

In accordance with the principles of the invention, an improved method and apparatus are provided for determining biomechanical parameters of a human joint. In accordance with the principles of the invention, a data base is acquired containing biomechanical parameters from a plurality of patients. To obtain the data base, biomechanical parameters for each patient are obtained. Each patient is trained to move his/her head in a predetermined manner which is in a plane of motion selected from a plurality of predetermined planes of motion. While the patient moves the joint in the designated plane of motion biomechanical data is gathered pertaining to the instantaneous helical axis of rotation of the cervical spine. The data base may then be used to classify the biomechanical parameters for subsequent patients. In addition, clinical information relative to each patient is obtained. The biomechanical data and the clinical information are combined as a model for the patient. Based upon that model, the status of the patient's cervical spine is classified.

In accordance with one aspect of the invention, the patient is trained to move his/her head in a plane of motion of flexion/extension during which biomechanical data is gathered for subsequent evaluation of the cervical spine of the patient.

In a system utilized in conjunction with the invention, a training aid is utilized to train the patient to move in a predetermined manner in a predetermined plane of motion for the gathering of data from which the kinematic function of the patients cervical spine may be determined. In accordance with the principles of the invention, data is gathered by the use of two positional sensor markers worn by the patient. A position monitoring system is utilized in accordance with the invention to determine the relative positions of the two sensors during the times that the patient moves his/her head in accordance with the predetermined manner to collect data relative to parameters of interest to the kinematic function. Parameters relating to specific aspects of the kinematic motion are derived from the data and are utilized to provide a biomechanical model of the patient's motion. Still further in accordance with the invention, the parameters include at least one parameter pertaining to each of position, orientation, speed and path in the selected plane of motion.

Still further in accordance with the invention, one sensor is worn by the patient at a predetermined reference point on the patients body in the vicinity of the cervical spine. Still further in accordance with the invention the second sensor is worn on the patient's head at a predetermined position.

Further in accordance with the invention, apparatus is provided for determining the three dimensional positions of the two sensors as the patient moves.

Further in accordance with the invention, apparatus is provided for training the patient to move in a predetermined manner and after the patient is trained to move in the predetermined manner, the patient moves voluntarily in the predetermined manner while data relative to the patient movement is gathered from the sensors. In an illustrative embodiment of this invention, a linear array of lights is provided and operated so as to train the patient to move his/her head at a predetermined velocity in a predetermined plane of motion. In the illustrative embodiment of the invention, the array of lights is oriented vertically and is used to train the patient to move his/her head in flexion-extension at a predetermined velocity. After the patient has followed the lights at the predetermined velocity, the patient voluntarily moves his/her head in flexion-extension voluntarily in approximation of the predetermined velocity.

The light array includes uniformly spaced lights along each arm of the array. The lights are illuminated in a predetermined manner. In accordance with the principles of the invention, the starting point for each line of axial movement starts at the center of the grid. The lights on the grid array illuminate from the center of the array to one extreme of the axis, then back through the center of the grid to the opposite end of the axis and back to the center staring point of the grid. The speed at which the lights are energized is chosen such that the angular velocity at which the patient moves his/her head will be constant through the full range of motion. After the patient has followed the light movement along an axis, the patient then voluntarily moves his/her head in the learned predetermined manner.

Still further in accordance with the invention, the apparatus includes a pointer device which is worn on the patient's head and which is used in conjunction with the light array to provide the patient with real time feedback as to the position of the patient's head relative to the light movement.

Prior to this invention, there existed no data base of biomechanical parameters for the human cervical spine.

BRIEF DESCRIPTION OF THE DRAWING

The invention will be better understood from a reading of the following detailed description taken in conjunction with the drawing in which like reference designators are used to designate like elements, and in which:

FIG. 4 is a perspective view of a patient wearable device in accordance with the principles of the invention;

FIG. 5 is a front planar view of the frame of the device of FIG. 4;

FIG. 6 is a front planar view of the device of FIG. 4;

FIG. 7 is a side view of the device of FIG. 4;

DETAILED DESCRIPTION

Figure 1:
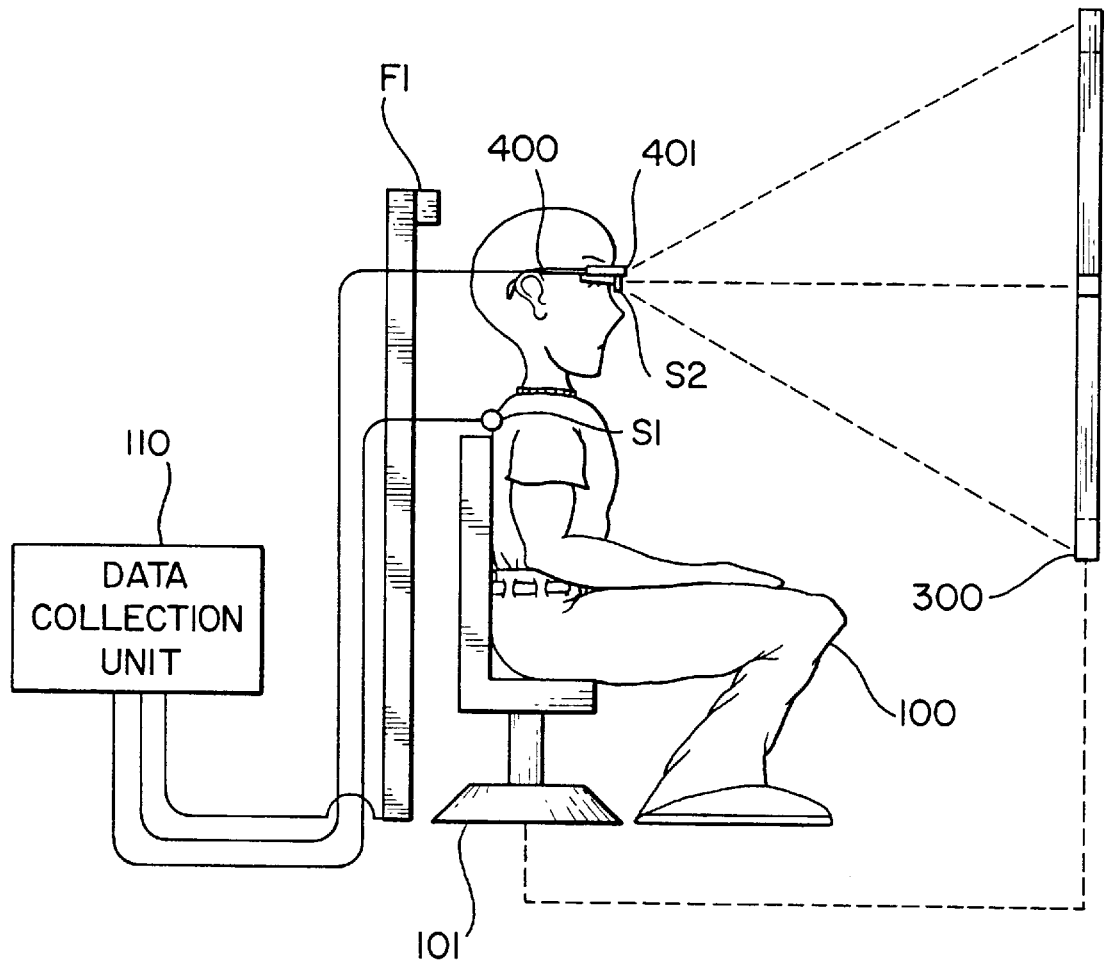
FIG. 1 illustrates a system in accordance with the principles of the invention.

In reading the following detailed description, certain terms are utilized for which definitions would be helpful. Accordingly, the following terms are defined as set forth next to them:

Axial rotation—Rotation at about the midline of the body (horizontal, left to right).

Cervical lateral bending—Motion of the cervical spine that occurs in the frontal plane around the anterior-posterior axis.

Cervical flexion/extension—Motion of the cervical spine that occurs in the sagittal plane around the medial-lateral axis (vertical, up and down).

Cervical rotation—Motion of the cervical spine that occurs in the transverse plane around a longitudinal axis (horizontal, left to right).

Cervical spine—The first seven (7) segments of the vertebral column starting at C1 located at the top of the spine and extending to but not including the first thoracic vertebra.

Extension—The bending of a joint that causes two adjoining bones to move away from each other. In the cervical spine, this refers to the bodies of the adjacent vertebra.

Flexion—The bending of a joint that causes two adjoining bones to move closer together. In the cervical spine, this refers to the bodies of the adjacent vertebra.

Frontal plane—The plane that divides the body into front and back halves.

Lateral bending—Motion that occurs in the frontal plane around the anterior-posterior axis.

Sagittal plane—The vertical plane that proceeds from the anterior to the posterior aspect of the body.

OVERVIEW

In accordance with the invention, novel methods and apparatus are described in which biomechanical parameters of joints may be determined. The biomechanical parameters are obtained while the joint is moved by the patient in a predetermined pattern of movement. From the biomechanical parameters obtained during motion of the joint, the quality of a joint may be determined from a biomechanical basis. To further provide beneficial uses of these biomechanical parameters, clinical information from patients may also be utilized to provide for a model of the patient's joint which will provide an indication of the healthiness of the joint. The inclusion of clinical information allows for a further weighting or adjustment of the modeling to take into account the subjective nature of an individuals perception of the quality of his/her joint which is being studied.

The illustrative embodiment of the invention provides for the determination of biomechanical parameters for the cervical spine as well as the clinical evaluation thereof and combines the biomechanical parameters and the clinical evaluation for each patient into a statistical based model which permits categorization of the patient into having a healthy or normal cervical spine, an unhealthy or abnormal cervical spine, or having symptoms which are inconsistent with the biomechanical parameters.

As part of the methodology utilized in the illustrative embodiment, biomechanical data was obtained for a data base which provides a statistical basis for the categorization of patients. To obtain the data, a data collection methodology and apparatus were developed.

DATA COLLECTION

The data collection technology used in the illustrative embodiment utilizes a three-dimensional position location system in which at least one sensor is tracked in three dimensions on a real time basis. Sensor technology of this kind is commercially available from Polhemus, Incorporated. Systems of this type are described in U.S. Pat. No. 5,453,686, for a Pulsed-DC Position and Orientation Measurement System; U.S. Pat. No. 3,868,565 for an Object Tracking and Orientation Determining Means, System and Process; and U.S. Pat. No. 4,054,881 for a Remote Object Position Locator. Such sensor systems typically have a source that includes a plurality of concentrically positioned orthogonal field generating antenna for generating a plurality of electromagnetic fields. The position and orientation of an object relative to a referenced coordinate frame may be determined utilizing a source having a plurality of field generating elements that generate electromagnetic fields and a remote sensor which detects the generated fields. Specific details of such an arrangement are shown and described in the aforementioned patents and the disclosures of the '686, '565 and '881 patents are hereby incorporated by reference.

As should be evident to those skilled in the art, the following detailed description of a preferred embodiment of the invention which is directed to an arrangement for the determination of biomechanical parameters of the cervical spine does not limit the applicability of the invention. The invention may be equally applied to other joints and the principles described hereinafter are equally applicable to such other joints.

Turning now to FIG. 1, a patient for whom data relevant to biomechanical parameters during kinematic motion of the cervical spine is to be determined is positioned in a chair 101 which in the illustrative embodiment is positioned a predetermined distance "d" from a movement training guide 300. A first marker or sensor "S1" is located at a predetermined position on the patient on one side of the joint for which biomechanical parameters are to be determined. That predetermined position is located along the cervical spine of the patient and, in the illustrative embodiment directed to the cervical spine, is positioned on the upper back. A second marker or sensor "S2" is placed on the patient at a second predetermined position relative to the joint. In the illustrative embodiment of the invention the second sensor S2 is worn by the patient above the bridge of his/her nose. The sensor S2 is supported on a headpiece or eyeglass-type structure or a patient wearable unit 400. In addition, the eyeglass-type structure, or patient wearable unit 400, carries a laser pointer 401 disposed in a predetermined position on the patient wearable unit 400. The patient wearable unit 400 carries a bubble vial as an aid to position the patient to an initial position in relation to the patient's posture and horizontal plane. A field generating unit "F1" is disposed in the proximity of the patient. The field generating unit F1 is substantially that described in the aforementioned patents. The field generating unit F1 as well as the sensors S1 and S2 are coupled to a data collection unit 110. The data collection unit 110 is utilized to gather data from which the three-dimensional spatial positions of the sensors S1 and S2 may be determined on a real time basis.

By way of overview and as will be described in further detail below, the patient 100 will move the joint of interest in a predetermined manner. In this instance, because the joint of interest is the cervical spine, the patient will move his/her head in predetermined planes of motion at a predetermined desirable velocity. While the patient 100 is moving his/her head in the predetermined planes of motion, signals are gathered by the data collection unit 110 from sensors S1 and S2. The signals are used to produce data representative of the three dimensional positions of the sensors S1 and S2. The placement of the sensors S1 and S2 on the patient's body is dependent upon a determination as to what body segments are to be characterized as rigid body segments for purposes of the dynamic analysis which will be performed on the data obtained from the sensors.

Figure 2:
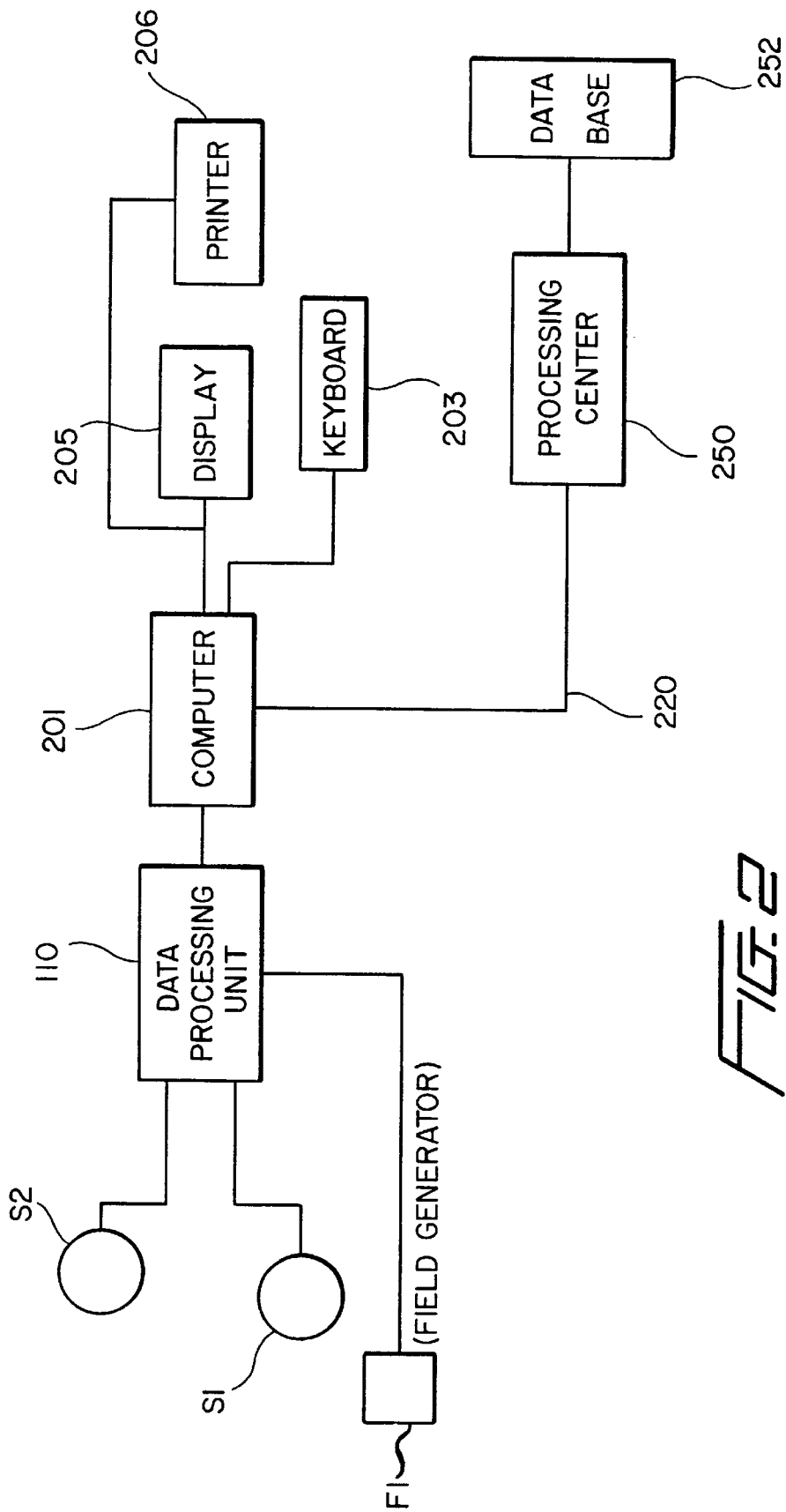
FIG. 2 is a block diagram of a the system of FIG. 1.

Turning now to FIG. 2, a system in accordance with the invention is shown in block diagram form. To determine the biomechanical parameters of a joint or the kinematic function of the cervical spine, the sensors S1 and S2 are placed on the patient's body. As noted above, sensor S1 is in the illustrative embodiment, placed on the patient's body in the or the upper back of the patient and the sensor S2 is carried on the patient by having the patient wear patient wearable unit 400. During the time that data is to be gathered from the sensors, the field generator F1 provides a reference field which is coupled to sensors S1 and S2. Operation of the sensors in conjunction with the reference field is described in the aforementioned patents and will not be repeated here. The data collection unit 110 receives signals from the sensors S1 and S2 and these signals are sampled at predetermined sampling rates. At each sampling time, signals from the sensors S1 and S2 are sampled. The data collection unit 110 generates data from the signal samples which identifies the position of each of the two sensors S1 and S2 in space with respect to a central coordinate system defined by the field generated by the field generator F1. This produces three-dimensional position coordinate data for the sensors S1 and S2 at each time sampling instant. The sampling occurs at a predetermined rate and in the preferred embodiment is performed at the rate of 60 Hz. The data obtained from sensors S1 and S2 provides information which is processed into biomechanical parameters that in turn are used to determine the kinematic function of the patient's neck. The data collection unit 110 provides its data representative of the relative position and rotation of the two sensors.

The data output from the data collection unit is provided to computer 201 which processes the data in accordance with the software routines to derive the velocity of motion, the coordinates of location for a parameter known as the instantaneous helical axis, and the orientation of the helical axis with respect to Eulerian angles. The data is processed to determine accelerations occurring with respect to movement of the instantaneous helical axis and the range of motion. For each time sample, ten data points are determined. The data points include the location of the sensor with respect to a specific axis, i.e., the primary axis being tested at that instant in time; an x coordinate, a y coordinate and z coordinate with respect to the center of mass over referenced points; the instantaneous velocity; the instantaneous acceleration; direction cosine, or what has been described as the unit vector cosines for x, y, and z angular orientation of the axis; and shift speed. The instantaneous helical axis is obtained by utilizing the techniques which have been described in the prior art by H. J. Woltring, as well as those described in the aforementioned patent to Arlan W. Fuhr. The data points are then processed by an additional software processing package which calculates a predetermined set of biomechanical parameters from the data points.

The biomechanical parameters may be grouped into four categories of particular stastical significance, i.e., the categories of position, orientation, speed, and path. At least one parameter is utilized from each of the four categories to create a statistical model for the patient's movement in the plane of motion in which the patient moves, e.g., in the case where the cervical spine is the structure of interest, the sagittal plane is the plane of interest. The system shown in FIG. 2 also includes a keyboard 203, a display 205 and a printer 206. It should be noted that the computer 201, keyboard 203 and display 205 are typically co-located with the data collection apparatus shown in FIG. 1. The printer 206 may or may not be co-located at the same location. Still further in accordance with the invention, the parametric information generated by the computer 201 is further processed. That further processing, in an embodiment of the invention, occurs at a separate processing center 250 which has associated with it an extensive data base 252 of biomechanical parameter information for patients. The computer 201 communicates with the processing center 250 over any one of a number of means. The data may for example be transported from the computer 201 to the processing center 250 on a tangible medium such as a CD ROM or floppy disk. Alternatively, the data may be transmitted modem and telephone line/data link or in the illustrative embodiment, communication between the computer 201 and the processing center 250 is via the Internet. Further details about processing of the parameters generated by the computer 201 will be presented below.

Figure 3A:
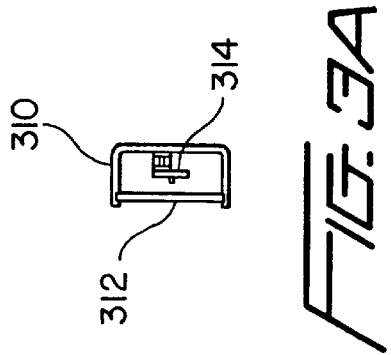
FIG. 3A is a cross-section of a portion of the structure of FIG. 3.
Figure 3:
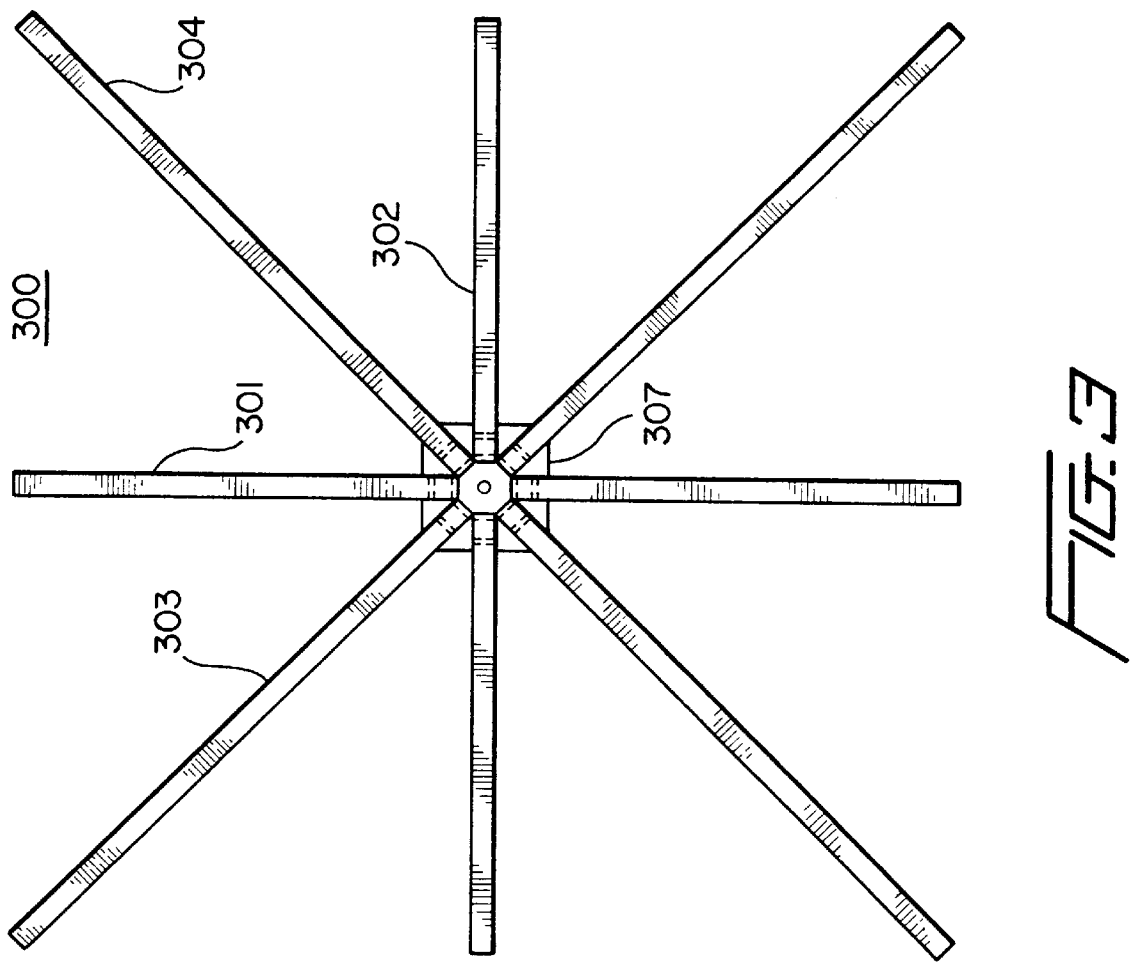
FIG. 3 illustrates a grid of lamps in accordance with the invention in which lamps are selectively illuminated to train the patient to move his/her head at a predetermined angular velocity.

Turning now to FIG. 3, the equipment for use in the present invention further includes apparatus which is utilized to train the patient to perform a predetermined movement at a predetermined speed. In the illustrative embodiment, an array of lamps 300 is utilized in which the lamps are arranged so as to provide the patient with a guide as to what type of motion is to be performed and at what speed. The array 300 includes a vertical linear array 301, a horizontal linear array 302, a left oblique array 303, and a right oblique array 304. The linear arrays, 301, 302, 303 and 304 are coupled together at a center hub 307. The center hub provides a neutral point as described below. Each linear array in the illustrative embodiment is arranged as a channel 310 having a transparent or translucent cover 312 with a reflection reducing overlay captured between the legs of the channel 310. Disposed within the channel are lights or lamps. The lights or lamps in the illustrative embodiment are light emitting diodes which are carried on printed circuit boards 314. Electronic circuitry which is not shown is utilized to control the operations of the lamps in the array. Only one of the linear arrays, i.e., one of the vertical, horizontal, left oblique or right oblique, is operated at a time. In operation, the lights are operated in a sequential manner so as to give the appearance of a moving light and thereby provide an indication to the patient as to the direction and speed for movement of the joint of interest. In short, the patient is to follow the movement of an illuminated light by moving his/her head such that a laser pointer which the patient is wearing follow the moving light. The linear arrays are sized such that the patient, when moving his/her head to follow light movement from one end of a linear array to the other end of the linear array will move his head through an angular motion of up to approximately 50 degrees in either direction from a neutral center position. The operation of the linear array is such that the patient is instructed to view the array and to follow the movements of light in the array. To assure that the patient moves his/her head at a constant angular velocity, the sequence of operation of lamps or the lamp spacing is such that operation of the lights will produce a constant angular velocity as projected back to the patient. The lamps may, for example, be uniformly spaced and the timing with which the lamps are energized varies as a function of the distance of each lamp from the center or neutral point of the array. Although the aid 300 is shown as having separate assemblies 301, 302, 303 and 304, it should be apparent that a single linear array such as that of 301 may be utilized and that singular angular array rotated to the various positions shown in FIG. 3 as fixed linear arrays. In addition, rather than have the linear arrays arranged to be in a single plane, the linear arrays may be curved toward the patient.

Turning now to FIGS. 4, 5, 6 and 7, the patient wearable unit 400 is shown. The patient wearable unit 400 is shown in perspective view in FIG. 4 and carried the sensor S2 as well as a laser pointer 401. The unit 400 includes a bridge portion 403 which is configured to be worn on the bridge of the nose of the patient. The unit 400 further includes temple portions 405 and 407. As shown in FIG. 5, the basic frame may be formed as an integral piece and subsequently bent to shape. A sensor S2 is disposed in the center of the unit 400 and a laser pointer 401 is carried at one of the temples. The unit 400 may be formed of plastic material such as acrylic and, in each instance, the laser is mounted on the same side of the unit 400, typically the right side. The unit 400 is secured to the patient's head by means of Velcro straps 409 which are carried at the ends of the unit 400. The laser 401 may be turned on or off by the system operator. The unit 400 is oriented to correspond simultaneously to a specific landmark and the horizontal plane.

In accordance with the invention, the patient wearable unit 400 as well as the training unit 300 jointly form a training aid which provides a visual indication to the patient of motion to mimic so that the patient easily understands the type of motion to be performed and the speed with which to perform a movement which is used as a standard movement for the gathering of biometric information relative to the joint being observed. For the illustrative embodiment the training aid is utilized to train the patient to move his/her head in a specific or predetermined manner at a specific or predetermined speed in one or more predetermined planes of motion. More specifically, it has been found that an extremely high degree of accuracy in determining kinematic function of the cervical spine results from having the patient move his/her head in a single plane of motion, i.e., the sagittal plane and at a predetermined speed.

In operating the system in accordance with the invention, the patient 100 is seated in the chair 101. Sensor S1 is positioned on the patient 100 on the patients upper back in line with the spine. The headset 400 is placed on the patient and the Velcro straps are fastened tight enough to prevent them shifting during movement. As noted above, the unit 400 includes a bubble level. By using the bubble level, the patient is positioned so that the so-called "Frankford" plane is in proper alignment. The Frankford plane is a horizontal line connecting the inferior, lateral margin of the orbit (the back corner of the eye) to the superior aspect of the Tragus of the ear (where the anterior flap of cartilage that covers the ear canal meets the front curvature of the ear connects to the top of the ear canal). The patient's head is raised or lowered until the Frankford plane is level. With the Frankford plane level, the laser 401 is adjusted so that it shines into the center or neutral point of array 300. When the patient is ready, linear array 301 is operated such that lights in the array are sequentially illuminated beginning at the center or neutral point of the array going to the bottom of linear array 301, then back up to the top of linear array 301, and then back to the center or neutral point of array 301. The lights are operated so as to give the appearance of a light moving at a predetermined constant angular velocity relative to the patient. The patient is asked to practice following the moving lights by moving his/her head so that the laser beam projected onto the linear array 301 or adjacent to the linear array 301 follows the illuminated lights. The patient's practice is limited to one or two cycles of motion. It has been determined that no more than two movements of the patient are necessary. At that point the array of lamps 300 is turned off, and the data collection unit 110 is activated. Without aid of the moving light arrangement being activated, the patient moves his/her head at the learned constant angular velocity from the neutral position to the bottom of linear array 301, i.e., minus 50 degrees, then back beyond the neutral position to the top of the linear array 301, i.e., plus 50 degrees beyond the central or neutral position of linear array 301 to the bottom (−50 degrees) and finally back to the neutral position. All the while that the patient is moving his/her head the laser pointer is on so that the laser pointer shows the patient where his/her head is orientated during the movement. The patient is instructed to keep the laser pointer shining on the array along the axis of interest. During the time that the patient moves in this manner, data relative to the sensors S1 and S2 is accumulated on a periodic basis based on the sampling rate.

Data collection unit 110 receives signals from the sensors S1 and S2 sampled in time. For each time sample, the computer locates the position of each of the sensors S1 and S2 in space with respect to a central coordinate system at the transmitter or field generator F1. This produces three-dimensional positional and angular coordinates in time for every instant of sampling. The sampling occurs at a predetermined rate and in the preferred embodiment is performed at a rate of 60 Hz. Data from sensors S1 and S2 provides information which is processed into parameters that are used to determine how the subject patient's neck works.

The 3-dimensional coordinates for two or more body segments are then equated to each other in such a way by computer data collection unit 110 such that the location of the center of mass of the first body segment and its orientation in space with respect to the center of the second body segment may be calculated. Each of those centers can be modified and adjusted according to user design to accommodate specific needs. These relative positions then of the two rigid body segments are presented as relative position and rotation data. The relative position and rotation data is then processed by computer 201.

Figure 8:
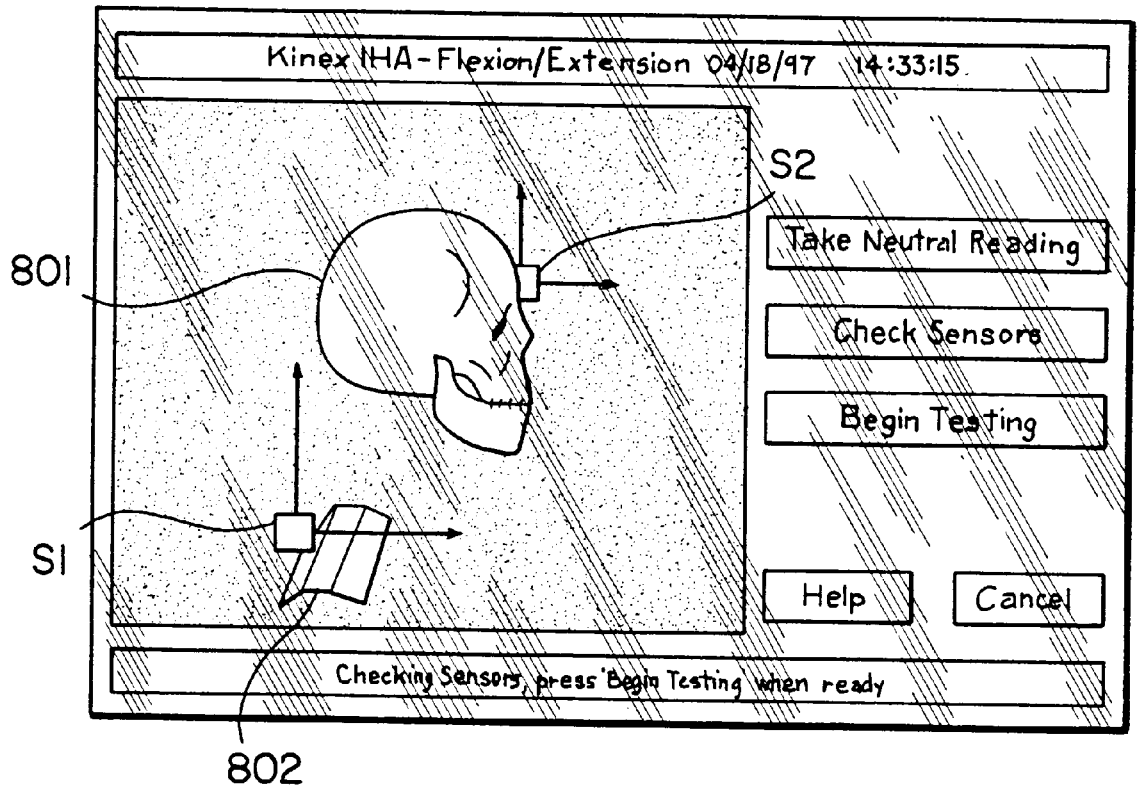
FIG. 8 is an illustrative screen display of a data capture screen on the display device of FIG. 2.
Figure 9:
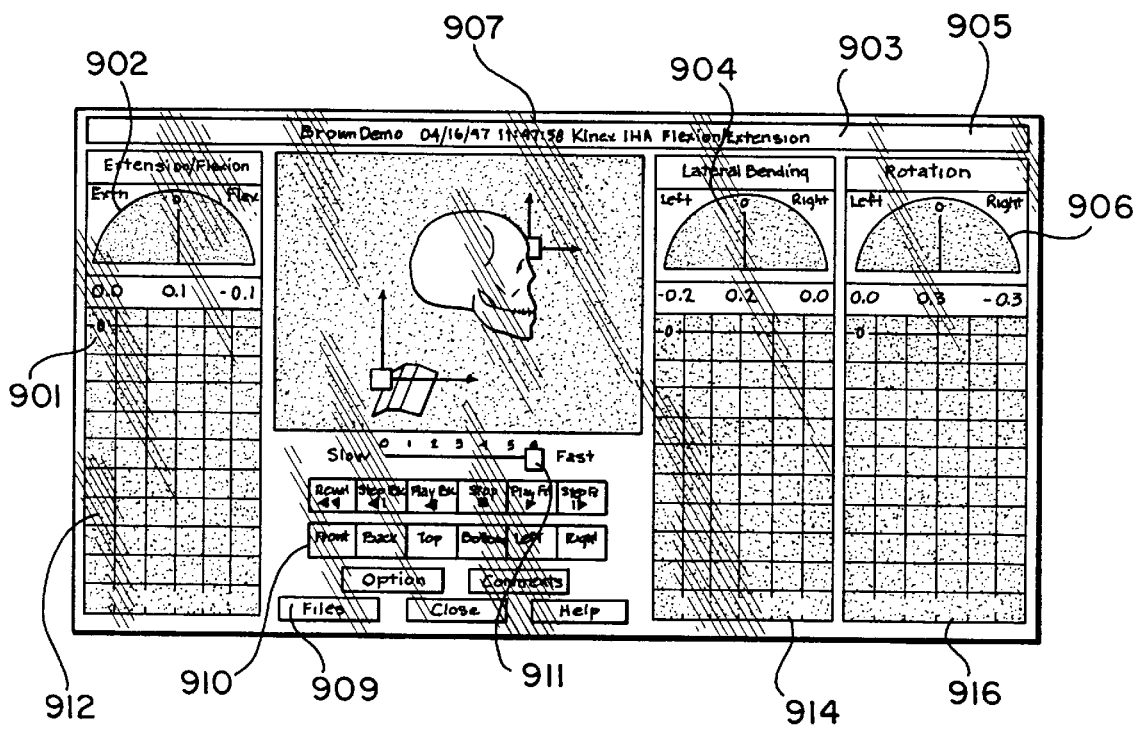
FIG. 9 is a motion display screen as displayed on the display device of FIG. 2.

At this point, display 206 in conjunction with the computer 201 may be used to view the collection of data, i.e., data capture. The computer 201 produces a display image on display 205. The display image during data capture is shown in FIG. 8 and includes a graphical indication of the position of the sensors S1 and S2. From a graphical standpoint, a picture of a skull or head 801 is shown along with a picture of the relevant portion of the spine 802. During the time the patient moves, the data captured from the sensors S1 and S2 is used to cause the display image to move in the same manner and speed that the data from the sensors S1 and S2 indicates. Thus the patient's motion as indicated by the data samples produces a visual display of the same motion of the representative figure, which in this case is a figurative skull and cervical spine, that reproduces the motion on the display as shown in FIG. 8. This enables the clinician who is monitoring the test activity to gain an immediate determination as to the viability of the data. The data is stored in a memory and can be replayed at the convenience of the clinician. After the data capture has been completed for the patient, the clinician may view the test data on a motion display screen as shown in FIG. 9. The image shown in FIG. 9 permits the clinician to view the playback of the data showing the motions of flexion/extension, in screen portion 901, lateral bending in screen portion 903 and rotation in screen portion 905. In addition, a display portion 907 which is comparable to the display shown in FIG. 8. In addition, the display includes a control portion 909 which has various cursor actuated control switches 910 for controlling the playback of the data. The motion display screen includes a slider 911 which controls the speed of the playback. This allows playback at real time or in slow motion. These graphical representations may be produced from the received data by utilizing any one of a number of software programs that are available for taking software data and reproducing it to have a predetermined image move in synchronization thereto.

Figure 10:
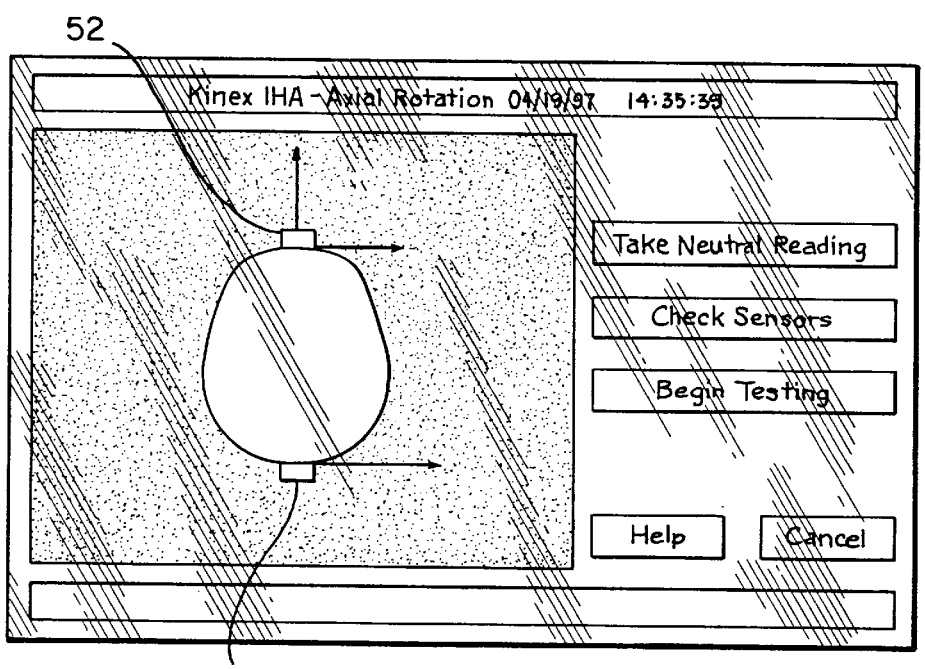
FIG. 10 is a second data capture screen display.

In addition to the flexion/extension data gathering, the patient may be asked to point the laser again at the center of the array, and the test may be repeated along the horizontal axis to produce axial rotation in the horizontal plane. During the time that axial rotation occurs, the display shown in FIG. 10 is displayed on the display unit 205. In FIG. 10, a simulation of the patient as viewed from above is shown. Again, for reference purposes, the display shows the sensors S1 and S2. As the data is being recorded, the display in FIG. 10 will show the patient's movements from center to the left, back through center to the extreme right, and back to center again. After this data has been collected, the clinician may again view a playback utilizing the motion display shown in FIG. 8.

After completing the axial rotation data capture, the patient may then be asked to move his/her head along the left oblique plane as represented by linear array 303. In that instance, a data capture screen similar to that shown in either FIG. 8 or FIG. 10 is utilized to verify operation. After the data has been collected, a motion display screen such as shown in FIG. 9 may be used to view the test data. Finally, the patient may be asked to move his/her head along the right oblique plane. In that instance, a display such as shown in either FIG. 8 or FIG. 10 may again be used so that the clinician can view the collection of data. After the data has been collected, the clinician may utilize a motion display screen to play back the patient's motion. After the data has been collected for flexion/extension, axial rotation, left oblique and right oblique have been captured and saved, processing of the data may occur. It should be noted that the only difference between the options of flexion/extension, lateral bending and rotation is the type of motion that the patient performs. The data capture display in FIG. 8 indicates at the top the type of test to be done. It should be noted that in this display, the clinician may click a cursor on the "take neutral reading" button after the patient has been positioned in a neutral position. The clinician may then click on the check sensors button and have the patient move his/her head around. In doing so, the clinician should see the skull representation and partial spine moving in synchrony with the patient. S1 is referred to as the static sensor because it moves the least during the test. If the patient moves only his/her head, S1 will remain static. S2 is referred to as a dynamic sensor because it is the one that shows the greatest movement. Once the sensors have been checked, the clinician may click on the begin testing portion of the display shown in FIG. 8. This signals the computer to begin capturing data. After the patient has completed one or more cycles of motion testing, the left mouse button is clicked to stop the test. As noted, the motion display shown in FIG. 9 is used to display various test results. The display includes seven main windows and a number of controls. The windows consist of representations of three needle-type gauges, three strip-type chart graphs and one three-dimensional window. The three-dimensional window 907 shows a fully rendered three-dimensional model in the form of a skull and partial spine representing the patient. The same model is used for each patient tested. The view of the three-dimensional model can be changed by the view direction control buttons 910 located below the window. Those buttons 910 control the view of the model from front, back, top, bottom, left or right. The display shown in FIGS. 8 and 9 is a right view display.

The gauge 902 and chart 912 to the left of the three-dimensional window display the primary motion, that is, the motion that was the primary focus of the data being viewed. For a cervical flexion/extension test, this would be flexion/extension. The two gauges 904, 906, and the charts 914, 916 to the right of the three-dimensional window 907 display the secondary motions. The secondary motions were not the primary focus of the test, but still may show some deviation. In a cervical flexion/extension test, the two secondary motions are lateral bending and axial rotation. The needle gauges 902, 904 and 906 show the current angle by the actual slant of the displayed needle.

The strip charts 912, 914 and 916 also show the current angle but as a line that deviates to either side of zero. One side represents extension or left, and the other side represents flexion or right. In the center, just above the chart, is a print out of the current value and degrees. To the left and to the right of this is a current maximum value for extension left and flexion right in degrees.

Turning back to FIG. 2, after the data for the patient has been obtained, it is transmitted via an Internet connection 220 to a processing center 250. At the same time that the biomechanical data is transmitted, a patient's Visual Analog Scale (VAS) and Neck Disability Index (NDI) scores are also supplied. The visual display portion of the data gathering function is an important aspect of the invention. It permits for almost instantaneous evaluation as to whether the data obtained appears to be valid or invalid.

DATA PROCESSING

Computer 201 processes the data in accordance with software routines described by H. J. Woltring to derive the velocity of motion, the coordinates of location for the instantaneous helical axis, and the orientation of the helical axis with respect to the eulerian angles. Woltring has published a software program which he developed as a program which provides calculation of instantaneous helical axis data. The helical axis data obtained from the data collection system of FIG. 2 is processed utilizing J. Woltring's approach for determination of the instantaneous helical axis. Existing Woltring based systems are very sensitive to noise properties of the environment and requires labor-intensive, cumbersome analysis. In accordance with one aspect of the invention it has been determined that the Woltring system may introduce backward propagating anisotropic noise. The Woltring filter relies upon the cross-correlation matrix and the statistical probabilities of the noise in the system. If the noise is not an uncorrelated white noise, the Woltring system will not provide optimal results. Noise characteristics of the various environments in which the data to be processed will be different. The Woltring filter efficiency continuously fluctuates. Specifically, it has been determined that during signal processing, the system introduces non-homogeneous, backward-propagating, isotropic noise on all data channels. That is, there are different amplitudes of noise on separate channels. In accordance with one aspect of the invention, it has been determined that the noise introduced by processing instantaneous helical axis data in accordance with the published Woltring software arrangements will be significantly reduced or eliminated by applying additional software filtering to the data processed by the Woltring software. In the illustrative embodiment a Butterworth filter is provided in the software processing of the data. The filtering is implemented in accordance with known software techniques for implementing filtering functions in software.

The collected data is then processed to determine accelerations occurring with respect to movement of the helical axis and the range of motion. Ten data points are determined for each time sample. Each time sample comprises the location of the head or the body segment orientation with respect to a specific axis, i.e., the primary axis being tested at that instant in time; the X coordinate, Y coordinate and Z coordinate with respect to the center of mass to the reference point; the velocity at that instant in time; the acceleration at that instant in time; and the direction cosines or what has been described as the unit vector cosines for X, Y and Z angular orientations of the axes; and the shift speed. The ten categories of data obtained for a patient are listed identified as: Z angle, PPX (piercing point x-axis), PPY (piercing point y-axis), PPZ (piercing point z-axis), acceleration, rotation speed, shift speed, unit X, unit Y and unit C. Those ten data points are entered into another software processing package which calculates 164 biomechanical parameters from the data points. The biomechanical parameters may be grouped into four categories of particular statistical significance with respect to at the least motions within the planes for which data is gathered, i.e., the categories of position, orientation, speed and path.

The instantaneous helical axis position represents the relative location of a mathematically defined landmark on the instantaneous helical axis with respect to the user selected reference point. The reference point selected on the basis of representing the upper torso as a rigid body in such a way as to affect advantages for evaluating neck function. However, it will be understood by those skilled in the art that although the illustrative embodiment of the invention is directed to determinations with respect to the cervical spine that the principles also apply to other joints and that the instantaneous helical axis position may be used to represent the relative location of a landmark positioned proximate other body joints for evaluating such other joints and the corresponding joint function.

Speed is defined as how rapidly the instantaneous helical axis translates or rotates in space. The orientation is defined by three values representing the Eulerian angles of the axis with respect to the user defined reference frames. Path is defined in the sense of a space curve.

There are many combinations of parameters selected from the four groups which are useable to generate a model. At least one parameter is chosen from each of the groups. These parameter types are used to create a statistical model for the plane of motion in which the patient moves, e.g., the sagittal plane.

The features of each of the parameters are relevant to one or more of the different planes of motion of interest. The parametric data recorded during the initial or start-up interval of the patient's motion and during the terminate or shut-down interval during the range of motion is ignored or truncated. The truncation removes the parametric data obtained in the initial portion of the range of motion which is an acceleration phase known to be error-prone. Similarly the truncation removes parametric data obtained in the final portion of the range of motion which is a deceleration phase also known to be error-prone. This truncation of the data obtained is also a feature of the present invention. It has been determined that failure to truncate the data obtained from the patient's movement during initial and terminal stages of movement of the joint can significantly and adversely affect the accuracy of the results obtained. After truncation of the data, the resulting parametric data are then filtered using criteria consistent with biologically consistent motion. The filtered parametric data is then analyzed with particular interest in partitioning the parametric data into segments related to what may be referred to as the initial phase and the second phase of motion.

The initial phase is unidirectional, e.g., it starts in the sagittal plane at one extreme of the chosen plane of motion, e.g., at full flexion position and goes to the other extreme of the chosen plane of motion, e.g., full extension position. The second phase begins at the other extreme, e.g., full extension and then goes back to the first extreme, e.g., full flexion. The parametric data for these movements is entered into the statistical model. This parametric data is examined for error sources, evidence of technical performance of the test being inadequate and drop-outs of data points such as happens with electronic data collection systems. Drop-outs are replaced with assumed data points based upon a linear extrapolation across the drop-out as long as there are no more than 3 consecutive points dropped out.

To develop a useful model, a dependent grouping variable was used.

The dependent grouping variable (as a function of the independent variables), upon which the model was based is a division of patients between "healthy", "unhealthy" (cervical spine related problem), and those patients for whom the cervical findings are inconsistent with the patient's self-report. This last category of patients may be referred to as "symptom amplifiers."

Independent variables (i.e. a function of the patient measures, ideally uninfluenced by the examiner) were selected from two sources. One source was the patient self-report of clinical information from a Neck Disability Index (NDI) evaluation completed on the day the biomechanical test was performed. The NDI is a patient's perceived functionality of the patient's neck. Results from descriptive statistical analysis suggested that this variable might give useful information to distinguish between groups. The second was a report known as the visual analogue scale (VAS). The VAS, while providing the perspective of the patient's perceived pain rather than the patient's perceived functionality, was strongly correlated with the NDI. Only the NDI was chosen for inclusion in the model of the illustrative embodiment based upon the impact of statistical bias (multicolinearity) that would occur from using both the NDI and VAS.

The other source of independent variables are instantaneous helical axis (IHA) parameters determined for cervical flexion/extension. The 164 parameters within the data base represent four different properties of IHA movement, i.e., location; speed; orientation; and path length. Within each grouping of variables, means and standard deviations were calculated to determine if clinically relevant differences between patient groups held between different sets of parametric data.

Testing was conducted with patients moving at different speeds. Results of the testing indicate that speed is a significant issue for many parameters. Thirty-eight subjects (24 unhealthy, 13 healthy, 1 symptom amplifier) were used to confirm the original model at two separate speeds. At a slow speed, correct classification of the patients into patient categories occurred at a rate of 68.4%. At a higher speed, correct classification into patient categories occurred at a rate of 81.6%.

Thus, in accordance with the invention, the patient moves through a range of motion. Parametric data is collected and, from the parametric data, four parameters are utilized to determine the biomechanical status of the patient's neck. The four parameters are subjected to discriminate function analysis utilizing conventional well known types of computer software to do so. In the illustrative embodiment a commercially available statistical package known as "Number Cruncher" is utilized. More specifically, the data is entered into the computer and the computer creates a biomechanical model for the patient. The computer creates weighting factors by discriminate function analysis and determines biomechanical probabilities from the weights that are in the model based upon parametric data for a plurality of patients that is maintained in a data base.

Each patient model included a clinical component, determined by the Neck Disability Index (NDI). The NDI was used on the hypothesis that it would be of value in differentiating asymptomatic, normal variants or pathologic changes in IHA mechanics. The hypothesis was based on an understanding from the literature on technology designed for comparable uses. Diagnostic imaging like radiography and MRI are known to reveal a tremendous number of asymptomatic pathologic conditions that are without clinical importance. Doctors are charged with the task of trying to determine whether the current symptomatology is relevant to the pathology found. For example, in a 1995 study using discriminant function analysis to identify low-back pain patients versus age and gender-matched controls via MRI, the sensitivity for disc herniation was 95.65% and the specificity was 23.91%. In the same study, for disc degeneration, the sensitivity was 95.65% and the specificity was 15.22%.

In our investigation for the biomechanical component alone, the sensitivity to finding a healthy versus an unhealthy subject was 87%, while the specificity was 28%. The addition of the NDI into the model provided a sensitivity of 87% and a specificity of 86%. In addition, in using both the clinical and the biomechanical components there is the opportunity to discriminate the third group for consideration—those patients where the intensity of the clinical symptoms is not matched by equally severe biomechanical pathology. That group has been called "symptom amplifiers." Reliable classification for the three groups, using the full model was statistically significant ($F=10.1$, $p=0.0000$).

All statistical assumptions for validity of the discriminant function analysis used were independently evaluated for each parameter, in addition to the NDI. All of the assumptions were met. The model using the related variables is one of several that are viable. However, an important aspect of modeling these variables is the inclusion of at least one parameter from each of the location, speed, orientation and path categories. The model has been confirmed in a second independent study with 85% accuracy in discriminating between groups.

In accordance with the invention, biomechanical determinations are combined with clinical information. To provide a model, the clinical information is, in the present embodiment, determined from either a VAS graph or an NDI questionnaire. Each patient fills out a questionnaire which pertains to the patient's self-perception of his/her neck function. One clinical determiner used is the VAS which is a 100 mm line. The patient marks an X on the line to indicate the relative intensity of pain felt. The NDI utilizes 10 questions, with 5 detractor questions.

The model obtained from the biomechanical data is accurate regarding the biomechanical function of the neck, but each individuals own perception of what is a normal kinematic function is variable. By way of explanation, an x-ray may reveal what appears to be tremendous problems in the neck as a result of degenerative joint disease, disk bending, or other indications of something that is not considered normal. However, the condition may be a normal part of aging in many ways, but it is abnormal as to an unimpaired condition. The x-rays thus may reveal a condition which could be considered abnormal but the patient may function beautifully and may not be in pain, but the function is aberrant compared to normal function. The equipment utilized in accordance with the invention will determine the existence of an abnormal function. Unless the clinical component is also considered, an aberration may be detected but the determination of the clinical function alone will result in a large number of false positive indications. This is because the method and equipment of the invention will find the smallest of the biomechanical problems and determine that the person is unhealthy on the basis of biomechanical problems. Such problems exist almost universally. Whether or not the problem actually matters or not, is a totally different issue. The neck disability index, NDI, is a measure of the patient's perceived sense of their disability. It provides an indication of what the patient feels he or she can or can't do. For example, the NDI answers such questions as: can the patient sit for an extended period of time without pain? Is the patient comfortable reading? Can the patient perform functions of daily living?

By utilizing the present invention it might be possible to help change patient behavior by training them to move more effectively and reduce the stress on weak points.

In an original study of 220 people, inclusion/exclusion criteria were studied. The inclusion criteria were patients who were over the age of 18 years old who had some form of neck pain as a primary complaint and a sample of subjects were selected for their absence of neck pain and neck pain history. Seventy-four percent completed intake questionnaires on their self-perception of pain severity and impairment. Attending doctors separately categorized the patients into subgroups of mild/moderate/severe/acute/sub-acute/chronic/recurrent. Presence of radiculopathy (nerve impingement) was also rated. Radiculopathy was defined as pain extending down the arm in a pattern consistent with specific disturbance. Reflexes may be reduced. Muscles may have lost strength. The investigation revealed that the doctors assessment correlated relatively well with the patient's self assessment. Patients may be categorized into different diagnostic subgroups of mild/moderate/severe and then as acute/subacute/chronic/recurrent for a total of 12 categories.

A test group of patients known to be "symptom amplifiers" was compared with a group of patients who were considered to be sincere. The perceived pain was much higher than that of those who were sincere. For the neck disability index NDI test the same results were obtained, i.e., symptom amplifiers had an average disability level of roughly 52%, and patients who were sincere had an average disability of roughly 34%, a statistically significant difference.

The predictive model is based on contrasting the clinical variables with the four different categories of biomechanical variables: helical axis placement or location, speed, orientation, and helical axis path. Because of multicolinearity, effects between the VAS and NDI and superior test indications, the neck disability index, NDI, was chosen for use in the model. Reliable discrimination was obtained for three different groups, i.e., healthy, symptom amplifier and unhealthy, at P.00000 and a correct classification rate of 84%. This compares to a correct classification rate by change alone of 46% using prior probability statistics.

The system of the invention had an 87% correct classification rate in contrast to a 66% accuracy rate for motion measure alone. Using a more standard cross-validation procedure, that is, by withholding one-third of the data by random, stratified draw, produces an 80% correct classification rate for two thirds of the patients. For the last third, there was a 77% correct classification rate, which, is well above chance and well in line with available statistics. If one looks at sensitivity and specificity for healthy versus unhealthy patients; that is, the chance of being categorized as healthy or the chance of being categorized as unhealthy, one will find a sensitivity for the complete model of 87% and a specificity of 86%. If one looks at the biomechanical motion parameters alone, there is a sensitivity of 87%, but a specificity of 28%. Such findings are reassuring as they reflect stress exposure with highly successful assessment measures. A tremendous amount of pathology exists that is nonsymptomatic. The literature shows that 25–30% of asymptomatic people will have a notable abnormality on CT or MRI. These findings, used in isolation from information on the person's clinical condition, would yield a large number of false positive tests. That is why the specificity of these imaging technologies is low at 28%. The present invention resolves this problem by including valid and reliable clinical information coupled with the biomechanical parameters of real function directly within the model. The result is a highly sensitive and highly specific device.

Every patient that makes up the model, as a result of being in the model, has a mathematical calculation for its discriminate functions for the parameters weighted according to the mathematics of how they hang together and best discriminate between the groups. Those weights are then applied to the new data as they exist. Each patient model is then identified as falling into one of three groups according to probability.

STANDARDIZATION

To provide a verification standard for the system operation, two calibration aids have been developed for use with the system of the invention. The first calibration standard is a hinged physical model consisting of two rigid structures. A first sensor is supported on one of the structures and a second sensor is supported on the second structure. With this arrangement relative positioning between two sensors can be replicated and verified. A second calibration model provides for more complex motions. The model utilizes a commercially available plastic spine mold. Ligaments are added by using elastic bands attached to the spine. The elastic in the illustrative embodiment are the commercially available bands known as theraband. The elastic bands provide for coupled motions of the spinal members which although are not exact models of actual patient spinal structures, are an approximation of the complexity of anatomical muscle-skeletal structure. By using the calibration model facet joints may be connected together to simulate or mimic fusion of solid. A comparison may be made of the kinematic function of normal motion versus motion when joints are fused. This thereby provides an arrangement that permits determining how various fusions translate into changes in the data obtained from kinematic motion analysis and thereby permit modeling of the kinematic function to provide predictable diagnostic capability. This thereby permits determination of predictive equations for accurate classification of patients.

As a result of the validation tests conducted relative to the model presented by the present invention it has been determined that quantification of cervical spine function using a model which reflects both patient perception and biomechanical parameters of instantaneous helical; axis motion offers substantial promise for greater objectivity in evaluating cervical spine patients. Although the invention has been described in conjunction with certain preferred embodiments and procedures, the present invention is not intended to be limited to those particular embodiments and procedures. In addition, those skilled in the art will appreciate that various modifications and changes may be made to the illustrative embodiments and procedures without departing from the spirit or scope of the invention. It is intended that the invention be limited only by the claims appended hereto.

What is claimed is:

1. A system for obtaining biomechanical data for the cervical spine of a subject, comprising:

data collection apparatus operable to obtain biomechanical data for said subject while said subject moves in a predetermined manner;

a memory coupleable to said data collection apparatus, said memory recording said biomechanical data substantially simultaneously with said data being obtained;

a data processor operable to access said recorded biomechanical data to generate display data; and a display unit operable by said processor to display a figure representative of said subject and responsive to said display data such that said displayed figure moves to mimic said subject movement.

2. A system in accordance with claim 1, wherein:

said processor operates said display unit to display said figure selectively in at least one of a plurality of views of said figure.

3. A system in accordance with claim 2, wherein:

said plurality of views include at least two of a right side view, a left side view, a front view, a back view and a top view.

4. A system in accordance with claim 3, wherein:

said display unit is operable to display a selected one of said views of said figure movement simultaneous with said subject movement.

5. A system in accordance with claim 1, wherein:

said displayed figure movement mimics said subject movement substantially concurrent with said subject movement.

6. A system in accordance with claim 5, wherein:

said processor operates said display to display simultaneous with said figure a graphical plot of said subject movement.

7. A system in accordance with claim 1, wherein:

said processor operates said display to display simultaneous with said figure a graphical plot of said subject movement.

8. A system in accordance with claim 1, wherein:

said processor generates said figure as a skeletal figure of a cervical spine and a skull.

9. A system in accordance with claim 8, wherein:

said processor operates said display unit to display said figure selectively in at least one of a plurality of views of said figure.

10. A system in accordance with claim 9, wherein:

said plurality of views include at least two of a right side view, a left side view, a front view, a back view and a top view.

11. A system in accordance with claim 10, wherein:

said display unit is operable to display a selected one of said views of said figure movement simultaneous with said subject movement.

* * * * *